(12) United States Patent
Ricci et al.

(10) Patent No.: US 8,075,630 B2
(45) Date of Patent: Dec. 13, 2011

(54) TRANSCUTANEOUS PORT HAVING MICRO-TEXTURED SURFACES FOR TISSUE AND BONE INTEGRATION

(75) Inventors: John L. Ricci, Middletown, NJ (US); Harold Alexander, Short Hills, NJ (US)

(73) Assignee: Bio-Lok International, Inc., Deerfield Beach, FL (US)

( * ) Notice: Subject to any disclaimer, the term of this patent is extended or adjusted under 35 U.S.C. 154(b) by 1498 days.

(21) Appl. No.: 11/127,949

(22) Filed: May 12, 2005

(65) Prior Publication Data
US 2005/0267591 A1    Dec. 1, 2005

Related U.S. Application Data

(63) Continuation-in-part of application No. 10/237,355, filed on Sep. 6, 2002, now abandoned.

(60) Provisional application No. 60/317,568, filed on Sep. 6, 2001.

(51) Int. Cl.
*A61F 2/02* (2006.01)

(52) U.S. Cl. ............... 623/23.74; 623/11.11; 623/23.44; 623/23.49; 604/175

(58) Field of Classification Search ............... 623/23.44, 623/23.74, 11.11, 23.49; 604/175
See application file for complete search history.

(56) References Cited

U.S. PATENT DOCUMENTS

| | | | | |
|---|---|---|---|---|
| 3,870,832 | A * | 3/1975 | Fredrickson | 600/25 |
| 4,498,461 | A * | 2/1985 | Hakansson | 600/25 |
| 4,606,329 | A * | 8/1986 | Hough | 600/25 |
| 5,122,114 | A * | 6/1992 | Miller et al. | 604/506 |
| 5,456,724 | A * | 10/1995 | Yen et al. | 623/23.49 |
| 5,562,670 | A * | 10/1996 | Brånemark | 606/32 |
| 5,607,607 | A | 3/1997 | Naiman et al. | |
| 5,645,740 | A | 7/1997 | Naiman et al. | |
| 5,746,720 | A * | 5/1998 | Stouder, Jr. | 604/117 |
| 6,210,376 | B1 * | 4/2001 | Grayson | 604/264 |
| 6,840,919 | B1 * | 1/2005 | Håkansson | 604/175 |
| 7,172,574 | B2 * | 2/2007 | Lundgren et al. | 604/93.01 |
| 7,766,881 | B2 * | 8/2010 | Reinmann | 604/175 |

* cited by examiner

*Primary Examiner* — David Isabella
*Assistant Examiner* — Javier Blanco
(74) *Attorney, Agent, or Firm* — Pillsbury Winthrop Shaw Pittman LLP

(57) ABSTRACT

A transcutaneous port includes a subcutaneous port section and a bone fixation section. The subcutaneous port section has upper portion which has an axial channel and a first micro-textured external surface, and a lower portion which has therein a transverse channel connecting to the axial channel. The bone fixation section has a transosseous collar portion which has a second micro-textured external surface, and a threaded shaft portion. The first and second micro-textured external surfaces include a multiplicity of alternating micro-grooves and ridges for tissue and bone integration. The transcutaneous port is surgically implanted into a site of a patient and a conductive wire is introduced from the axial channel to the transverse channel, and placed in the subcutaneous soft tissue and in contact with a neural signal source for transmitting neural signals to a prosthetic motor device.

6 Claims, 10 Drawing Sheets

TRANSCUTANEOUS PORT HAVING MICRO-TEXTURED SURFACES FOR TISSUE AND BONE INTEGRATION

CROSS REFERENCE TO RELATED APPLICATIONS

This application is a continuation-in-part of application Ser. No. 10/237,355, filed Sep. 6, 2002, now abandoned, which claims the benefit under 35 USC 119 (e) of the provisional patent application Ser. No. 60/317,568 filed, Sep. 6, 2001. All parent applications are hereby incorporated by reference by their entirety.

FIELD OF THE INVENTION

The present invention relates to a transcutaneous port for facilitating electronic communication between an amputation site and a prosthetic motor device. More specifically, the transcutaneous port has micro-textured external surfaces to enhance integration of the soft tissue and bone tissue with the transcutaneous port, which reduces microbial infiltration of the soft tissue site.

BACKGROUND OF THE INVENTION

Transcutaneous devices have application in many areas of medicine, these including such areas as bone stents or pins where it is necessary to stabilize fragments of a bone during a period of healing, medication-dispensing soft tissue implants such as those that require external access by the needle of a syringe, and neural interface devices that require both physical stability at an amputation and/or nerve injury site and an external electrical port to which a prosthesis may be attached. These unique and diverse requirements, of transcutaneous devices have presented long-standing challenges within the medical disciplines, in which they exist.

Most transcutaneous devices must satisfactorily address requirements at three levels, namely, bone interface stability, soft tissue stability, and suitable properties of an external portion thereof. Accordingly, in a successful transcutaneous device, it is necessary to obtain a stable, reliable and bacteria free interface to both the hard and soft tissue surfaces thereof.

In the field of peripheral nerve interface development to develop a stable, practically useful mechanism for obtaining motor information from lesioned peripheral nerves, conduct this information out of the body and effectively activate prosthetic motor devices requires a stable nerve and skeletal attachment interface and a transcutaneous access port.

Common problems in the existing transcutaneous ports include instability of the transcutaneous ports which results in detachment of the device from the nerves, or the site and microbial infiltration at the interface between the transcutaneous port and surrounding soft tissue, which also results in the detachment.

U.S. Pat. No. 5,607,607 (to Naiman et al.) teaches a transcutaneous implant which has a first and a second microtexturized surfaces provided on the outer circumferential surface of the implant, and separated by a barrier zone. The transcutaneous implant is to be implanted within soft issue in situ, and both microtexturized surfaces are used for enhancing integration of the implant with the soft tissue. This type of transcutaneous implant is not anchored into bone and has no involvement with bone tissue, and its stability in an amputation site is limited.

Therefore, there is a strong need in the field of peripheral nerve interface development for improved transcutaneous ports which enables integration of the device with surrounding soft tissue and bone tissue, hence, provides feasibility for long term use of the transcutaneous port in situ for providing electronic communication to prosthetic motor devices.

BRIEF DESCRIPTION OF THE DRAWINGS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

DETAILED DESCRIPTION OF THE INVENTION

In one aspect, the present invention provides a transcutaneous port which can be surgically implanted into a site in a patient's body and serve as a basis of electrical communication between a prosthetic motor device and an amputation or trauma site.

Figure 1:
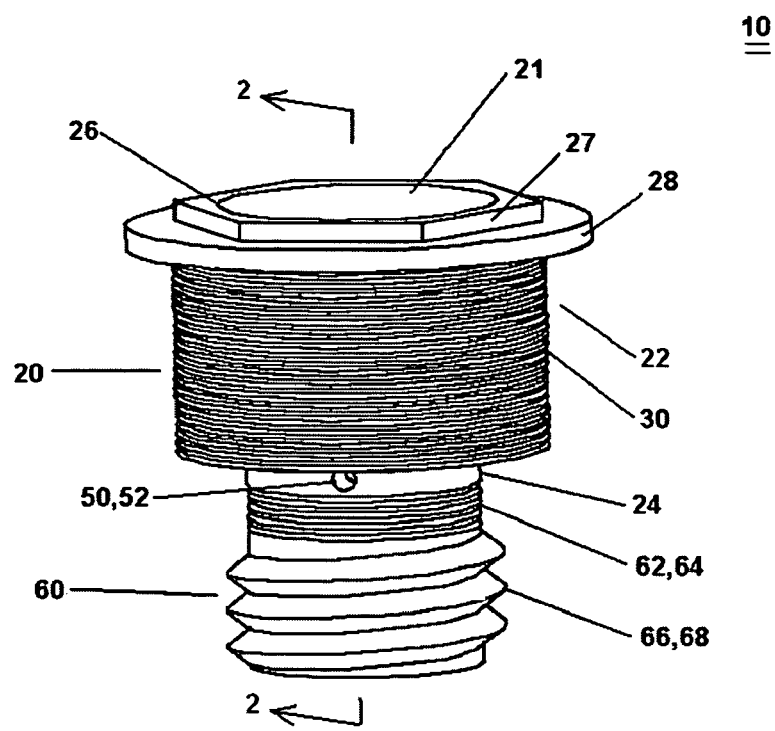
FIG. 1 is a perspective view of the transcutaneous port of one embodiment of the present invention.
Figure 2:
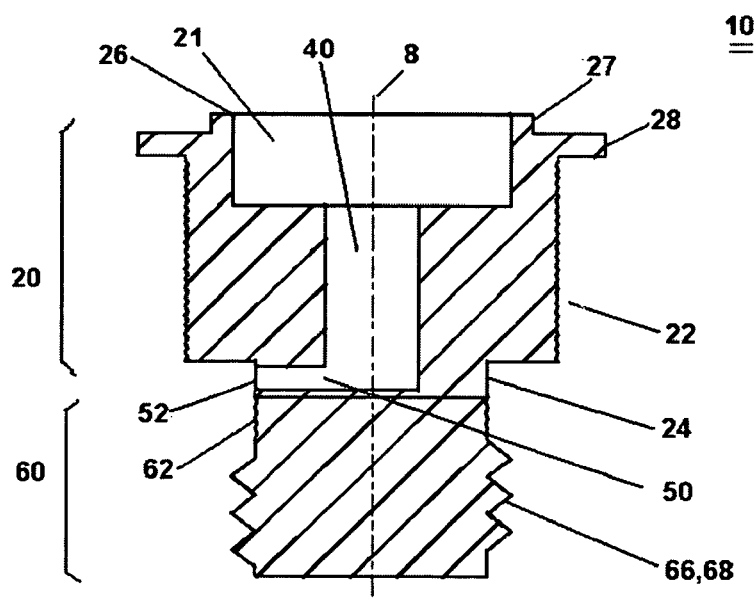
FIG. 2 is a cross sectional view along line 2-2 of the transcutaneous port shown in FIG. 1.

Referring to FIGS. 1 and 2, in one embodiment transcutaneous port 10 comprises subcutaneous port section 20 and bone fixation section 60. Both sections are essentially cylindrical. Subcutaneous port section 20 has an upper portion 22 and a lower portion 24. Upper portion 22 is larger in diameter than lower portion 24. As shown, subcutaneous port section 20 has an axial channel 40 extending from an upper end 26 of upper portion 22 into lower portion 24. Lower portion 24 has therein a transverse channel 50 disposed transversely to, and connecting with, axial channel 40. Transverse channel 50 has an exit 52 at one side of lower portion 24. Upper portion 22 also has a top flange 28 disposed around upper end 26. Optionally, upper portion 22 can further include a top chamber 21, which can receive a cap to seal axial channel 40 from exterior environment. In one configuration, top chamber 21 can have an internal thread (not shown) for a thread connection with the cap. Furthermore, top flange 28 has an engagement means 27 on the top surface thereof as an interface with a screw for screwing transcutaneous port 10 into the bone. In the embodiment shown in FIG. 1, the engagement means 27 is a hex head for engagement with a hex-head torque wrench.

Bone fixation section 60 integrally extends from lower portion 24 of subcutaneous port section 20. Bone fixation section 60 includes transosseous collar portion 62 and a threaded shaft portion 66 integrally extending from transosseous collar portion 62. Threaded shaft portion 66 has bone fixation thread 68 for anchoring transcutaneous port 10 inside bone, which can be made same as those on the transosseous implant known in the art. Preferably, the inner diameter of threaded shaft portion 66 is equivalent to the diameter of transosseous collar portion 62.

Figure 3:
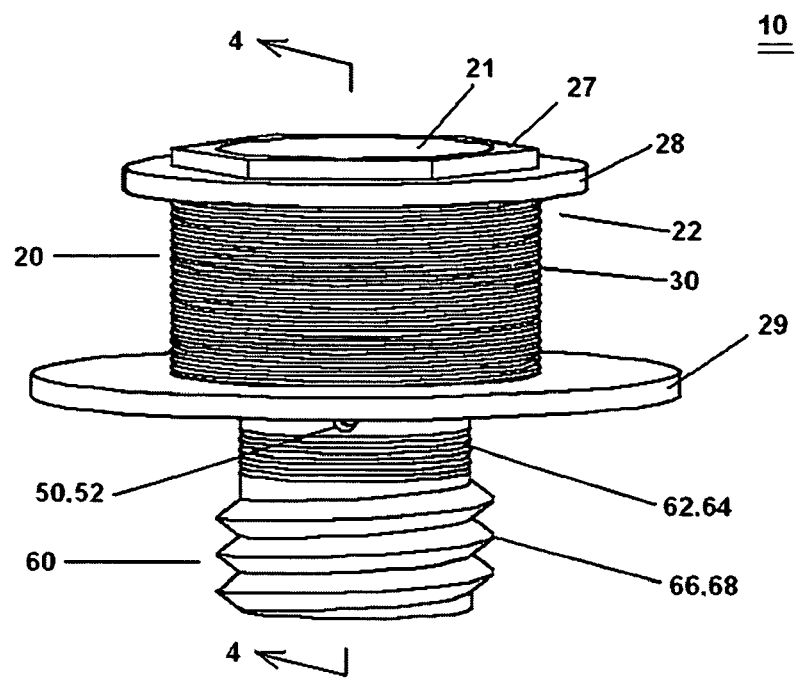
FIG. 3 is a perspective view of the transcutaneous port of a further embodiment of the present invention.
Figure 4:
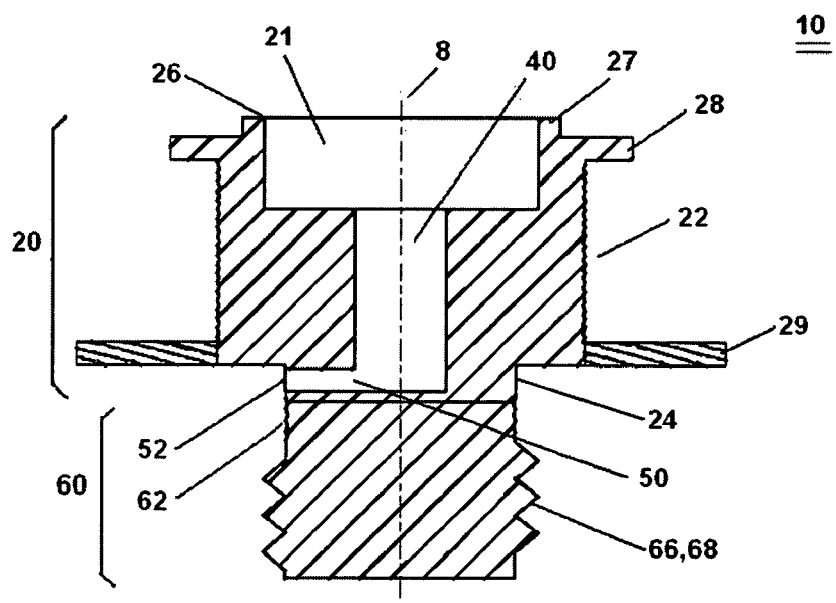
FIG. 4 is a cross sectional view along line 44 of the transcutaneous port shown in FIG. 3.

In a further embodiment shown in FIGS. 3 and 4, subcutaneous port section 20 can further comprise a middle flange 29 disposed around low end of upper portion 22. Middle flange 29 further increases the surface contact between transcutaneous port 10 and the subcutaneous soft tissue for enhancing stability of transcutaneous port 10 in the implant site. Preferably, the surface of middle flange 29 is porous, or rough-textured for enhancing tissue attachment.

The transcutaneous port can be made of titanium or titanium alloy, such as those materials used for surgical implants, known in the art. In an exemplary embodiment, subcutaneous port section 20 has a height approximately 2.5 mm, wherein upper portion 22 has a height approximately 2.0 mm, top flange 28 has a thickness approximately 0.25 mm, and lower portion 24 has a height approximately 0.25 mm. Axial channel 40 has diameter approximately 1.0 mm and transverse channel 50 has a diameter approximately 0.2 mm. The external diameters of upper portion 22, top flange 28 and middle flange 29 are approximately 4.0, 5.0 and 7.0 mm, respectively. Bone fixation section 60 has a height approximately 2.0 mm, and transosseous collar portion 62 has a diameter approximately 2.5 mm.

As shown, upper portion 22 of subcutaneous port section 20 has a first micro-textured external surface 30, and transosseous collar portion 62 of bone fixation section 60 has a second micro-textured external surface 64. In the embodiment shown in FIGS. 1 and 3, micro-textured external surfaces 30 and 64 comprise a multiplicity of alternating microgrooves 4 and ridges 6, which are further described in detail hereinafter. When in use, first micro-textured external surface 30 directly interfaces with subcutaneous soft tissue, while second micro-textured external surface 64 directly interfaces with bone tissue. In order to achieve superior integrations of subcutaneous port section 20 and transosseous collar portion 62 with soft tissue and bone, respectively, microgrooves 4 and ridges 6 in the first micro-textured external surface 30 preferably has different dimensions from microgrooves 4 and ridges 6 in the second micro-textured external surface 64.

FIGS. 8A to 8H illustrate various suitable configurations of microgrooves 4 and ridges 6, which can be used for forming micro-textured surface. Herein, the term "microgroove" refers to a groove having a width and a depth in the order of micrometers, more particularly having a width and a depth less than 50 micrometers.

Figure 8A:
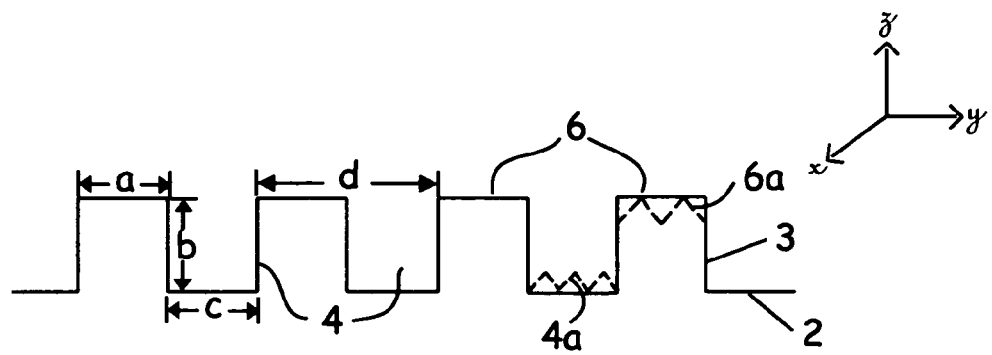
FIGS. 8A to 8H are diagrammatic cross sectional views of various configurations of microgrooves and ridges that can be used on the surfaces of the transcutaneous port.
Figure 8B:
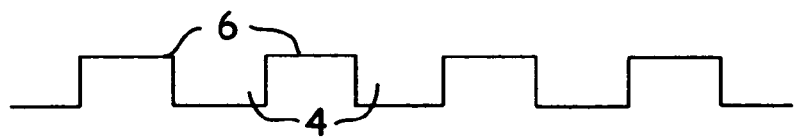
Figure 8C:
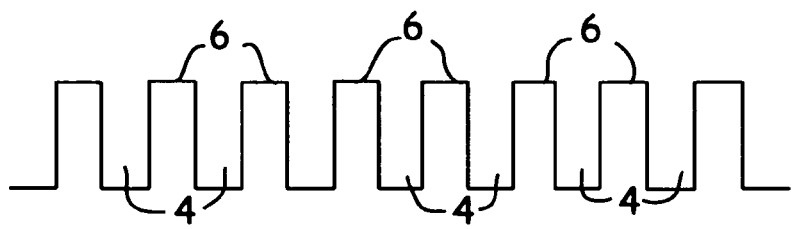

As shown, each microgroove 4 has a groove base 2 and a groove wall 3. The dimensions of the microgrooves 4 and ridges 6 are indicated by the letters "a", "b", "c" and "d". These configurations include those having square ridges 6 and square microgrooves 4 (FIG. 8A) where "a", "b" and "c" are equal and where the spacing (or pitch) "d" between adjacent ridges 6 is twice that of "a", "b" or "c". FIGS. 8B and 8C illustrate rectangular configurations formed by microgrooves 4 and ridges 6 where the "b" dimension is not equal to that of "a" and/or "c".

Figure 8D:
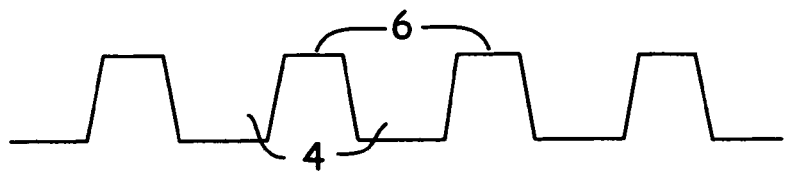
Figure 8E:
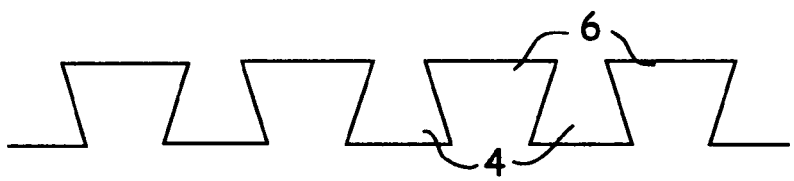
Figure 8F:
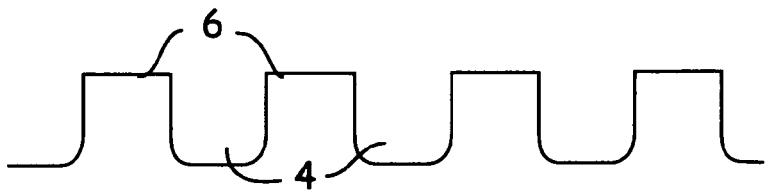
Figure 8G:
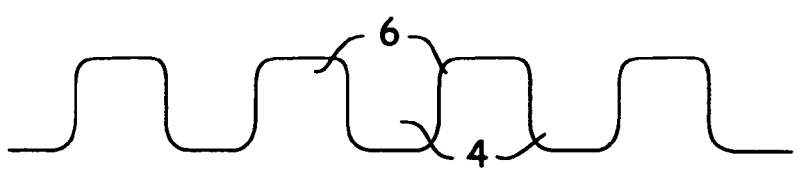
Figure 8H:
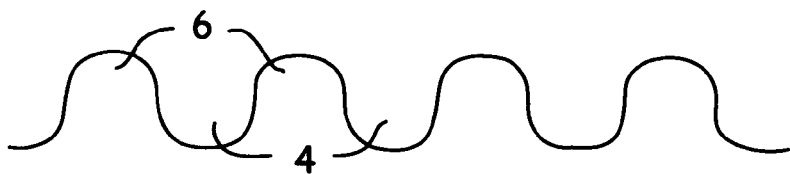

FIGS. 8D and 8E illustrate trapozidal configurations formed by microgrooves 4 and ridges 6 where the angles formed by "b" and "c" can be either greater than 90° as shown in FIG. 8D or less than 90° as shown in FIG. 8E. As shown in the above-configurations, each groove defines, in radial cross-section thereof, a relationship of the groove base 2 to the grove wall 3, which is in a range from about 60 degree to about 120 degree. In FIG. 8F, the corners formed by the intersection of dimensions "b" and "c" have been rounded and in FIG. 8G, these corners as well as the corners formed by the intersection of dimensions "a" and "b" have been rounded. These rounded corners can range from arcs of only a few degrees to arcs where consecutive microgrooves 4 and ridges 6 approach the configuration of a sine curve as shown in FIG. 8H. In all of these configurations, either the planar surface of the ridge 6; i.e., the "a" dimension, or the planar surface of the microgroove 4; i.e., the "c" dimension, or both can be corrugated as shown by dotted lines at 6a and 4a in FIG. 8A.

In the microgroove configurations illustrated in FIGS. 8A to 8H, the dimension of "c", i.e., the width of the microgroove, can be from about 1.5 μm to about 50 μm, preferably from about 4 μm to about 40 μm. In the trapozidal configurations as shown in FIGS. 8D and 8E, the width of the microgroove can be defined at the width at the half height of the microgroove. The dimension of "a", i.e., the width of the ridge, can be equal or different from "c" depending on the design needs. The dimension of "b", i.e., the depth of the microgroove, should be similar to "c" for the purpose of inhibiting smooth muscle cell proliferation.

The microgrooves shown in FIGS. 8A-8H can be arranged in various geometric patterns in different embodiments of the present invention, as illustrated in FIG. 9 to FIG. 22. More particularly, with reference to FIG. 9, the microgrooves can be in the form of an infinite repeating pattern of alternating microgrooves 112 and ridges 110. In the embodiment shown in FIG. 10, the microgrooves 114 and ridges 116 increase (or decrease) in width in the direction in perpendicular to the longitudinal axis of the microgrooves.

Figure 11:
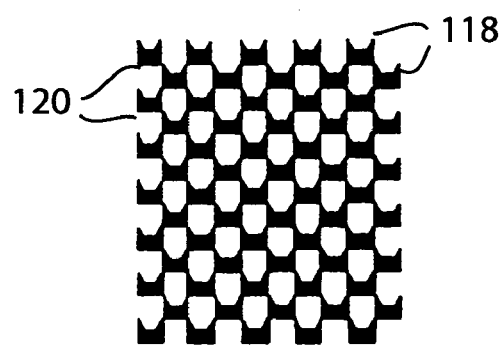
Figure 12:
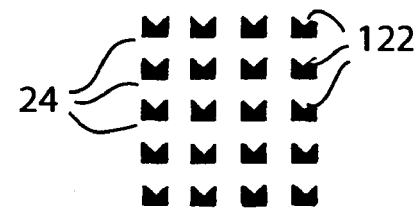
Figure 13:
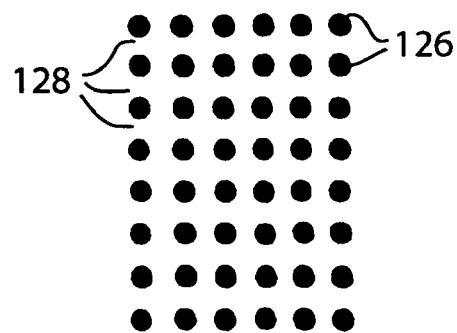

In the embodiment shown in FIG. 11, a surface pattern in which ridges 118 take the form of projections while grooves 120 take the form of recesses define a checkerboard configuration. The embodiment shown in FIG. 12 differs from that of FIG. 11 in that ridges 122 thereof form a bi-axial linear pattern. Similarly, grooves 124 of the embodiment of FIG. 12 define a matrix formed of recesses that may assume a number of geometries. In the embodiment shown in FIG. 13, circular depressions 126 define grooves or depressions while the areas there between, namely, spaces 128 define ridges or projections. It may, therefrom be appreciated that the terminology "alternating ridges and grooves," as used herein, encompasses a variety of micro-textured geometric patterns in which the ridges and grooves thereof while alternating relative to each other may themselves comprise one of a variety of geometries inclusive of channels, rectangles, parallelograms, squares, circles and ovals.

Figure 14:
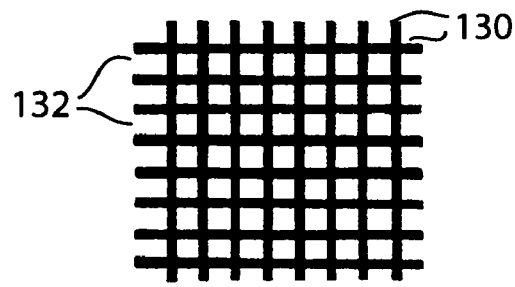
Figure 15:
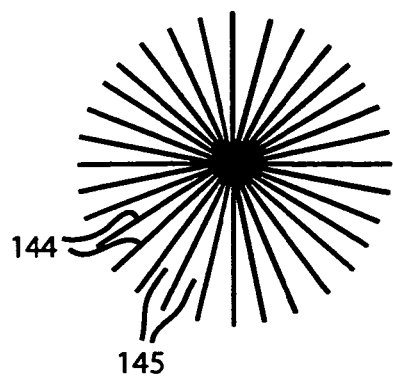
FIGS. 15 to 22 are diagrammatic plan views illustrating further geometric patterns in which the microgroove configurations FIGS. 8A-8H can be arranged.
Figure 16:
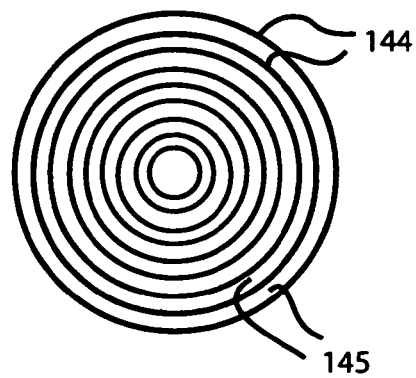
Figure 17:
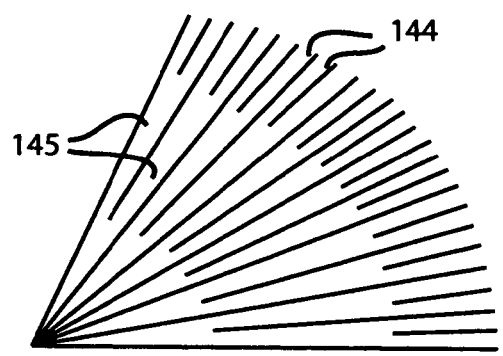
Figure 18:
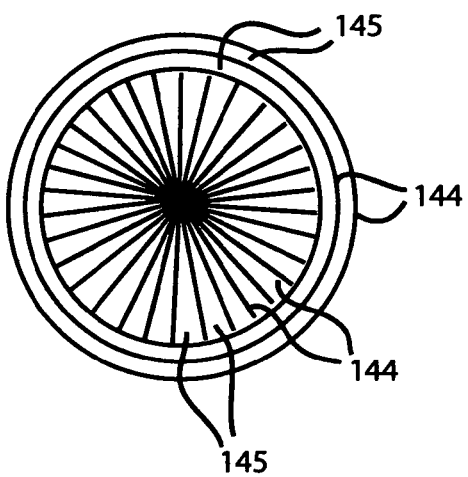
Figure 19:
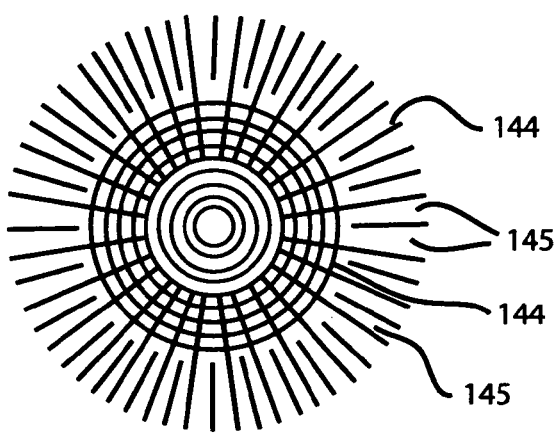
Figure 20:
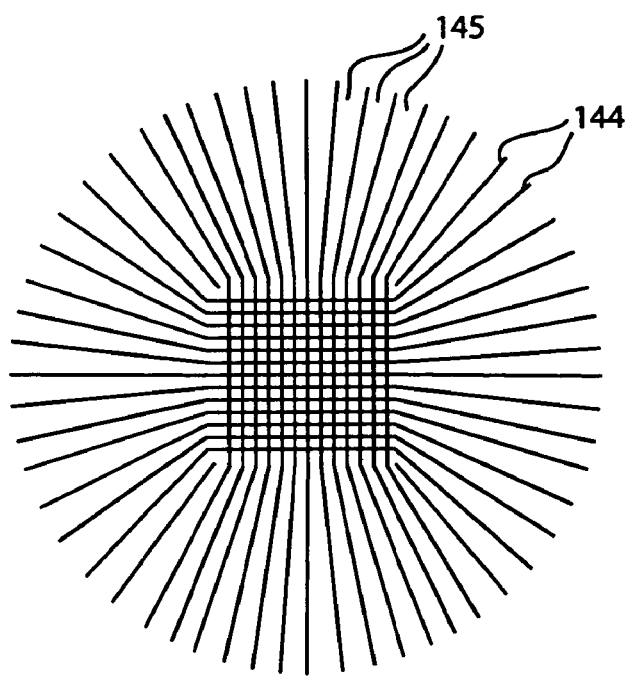
Figure 21:
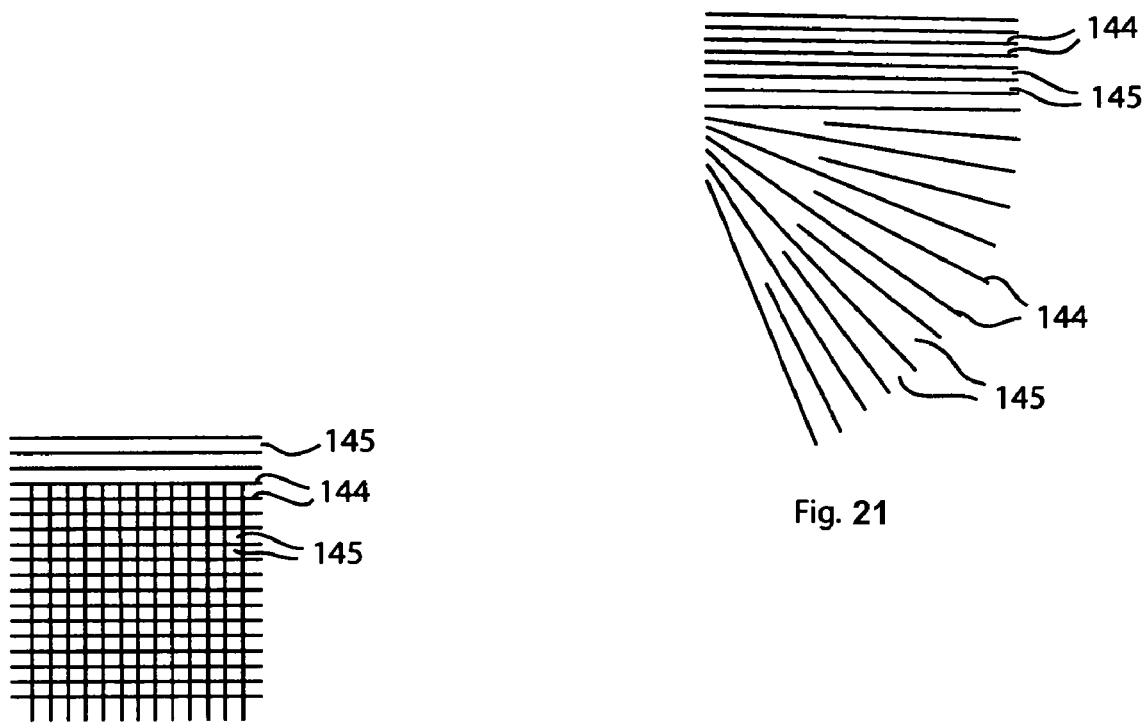

In the embodiment shown in FIG. 14, the geometric pattern is a grid like arrangement in which grooves 130 define a xy matrix which is etched into a surface 132 such that surface 132, when viewed relative to etched grooves 130, comprises ridges. From the embodiments of FIG. 9 to FIG. 14, it may be appreciated that the width (or diameter) of a given groove need not correspond to that of its respective ridge, providing such widths fall within the above-referenced range of about 1.5 to 50 microns with a depth in a range of about 1.5 to about 50 microns.

Figure 22:
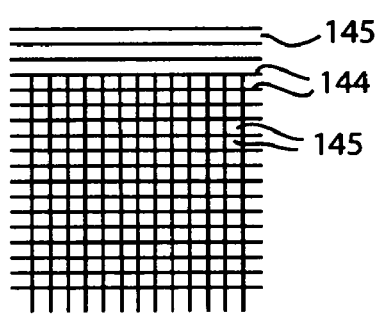
Figure 23:
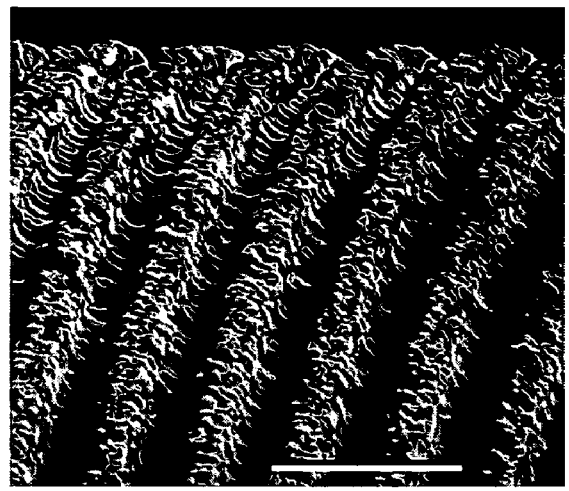
FIG. 23 is a photograph of the microgrooves and ridges of the micro-textured surface of the transosseous collar portion of the transcutaneous port illustrated in FIG. 1, wherein the bar equals 43 micron.
Figure 24:
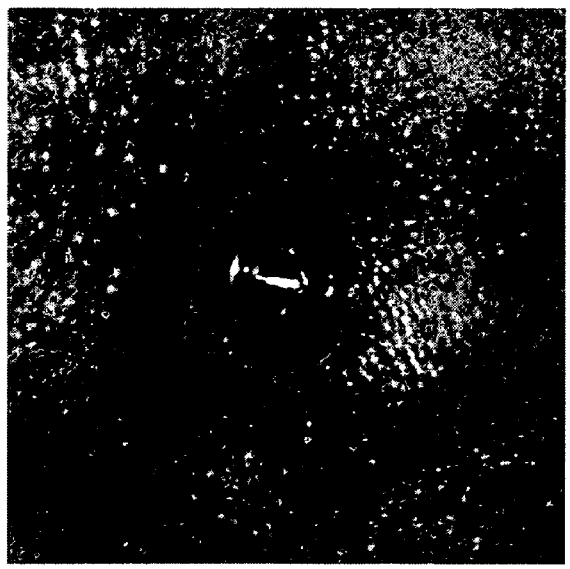
FIG. 24 is a photograph of a transcutaneous port illustrated in FIG. 1 in situ implanted in the body of a rat.

Furthermore, FIGS. 15 to 22 show additional geometric patterns that the microgrooves of FIGS. 8A to 8H can be arranged in the form of unidirectional, arcuate and radial patterns as well as combinations thereof. As shown, these geometric patterns include radiating patterns (FIGS. 15); concentric circular patterns (FIG. 16); radiating fan patterns (FIG. 17); radiating/concentric circular patterns (FIG. 18); radiating pattern intersecting concentric circular pattern (FIG. 19); an intersecting pattern surrounded by a radiating pattern (FIG. 20); a combination radiating fan pattern and parallel pattern (FIGS. 21); and, a combination intersecting pattern and parallel pattern (FIG. 22). In all these figures, the black lines indicate the grooves (144), and the white areas between the adjacent grooves indicate the ridges (145).

From the embodiments illustrated in FIGS. 8A to 8H, FIGS. 9 to 22, it will be appreciated that the external surfaces of upper portion 22 of subcutaneous port section 20 and transosseous color portion 62 can be provided with micro-textured surfaces having a multitude of geometric patterns, configurations and cross sections.

The above-described micro-textured surfaces can be produced by laser based technologies known in the art, for example the instrument and methodology illustrated in details in U.S. Pat. Nos. 5,645,740 and 5,607,607, which are herein incorporated by reference in their entirety.

It has been found that micro-textured surface having alternating microgrooves and ridges having width and depth in a range from about 1.5 μm to about 50 μm encourages ingrowth of soft tissue and bone tissue cells into the microgrooves, and achieves a strong integration of an implant having such micro-textured external surface with surrounding soft tissue or bone tissue. The ingrowth is directional along the pathway of microgrooves. Such surface property in controlling cellular growth has been illustrated in detail in U.S. Pat. Nos. 5,645,740 and 5,607,607, which are herein incorporated by reference in their entirety.

Furthermore, it has also been found that the preferential dimension of the microgroove, defined by width and depth of the groove, is different for different tissues. For example, the dental implants manufactured by Bio-Lok International, Inc., Deerfield Beach, Fla., which have a groove width about 8 micron in the region for soft tissue, and a groove width about 12 micron in the region for bone tissue, were clinically proved to enhance implant integrations with soft tissue and bone tissue, respectively, and were recently approved by the Federal Drug Administration for dental use.

Figure 9:
FIGS. 9 to 14 are diagrammatic plan views illustrating various geometric patterns in which the microgroove configurations of FIGS. 8A-8H can be arranged.
Figure 10:

In a preferred embodiment of the present invention, the co-parallel linear microgrooves and ridges, as shown in FIG. 9, are produced on both first and second micro-textured external surfaces 30 and 64, wherein microgrooves 4 and ridges 6 are in a direction perpendicular to the longitudinal axis 8 of transcutaneous port 10. Preferably, microgrooves 4 and ridges 6 of first micro-textured external surface 30 have a width in a range from about 4 to about 40 microns, and a depth in a range from about 4 to about 40 microns. Preferably, microgrooves 4 and ridges 6 of second micro-textured external surface 64 preferably have a width in a range from about 4 to about 25 microns, and a depth in a range from about 4 to about 25 microns. Furthermore, within each micro-textured surface, microgrooves 4 have a substantially equal width and depth, and ridges 6 also have a substantial equal width to microgrooves 4.

Figure 5:
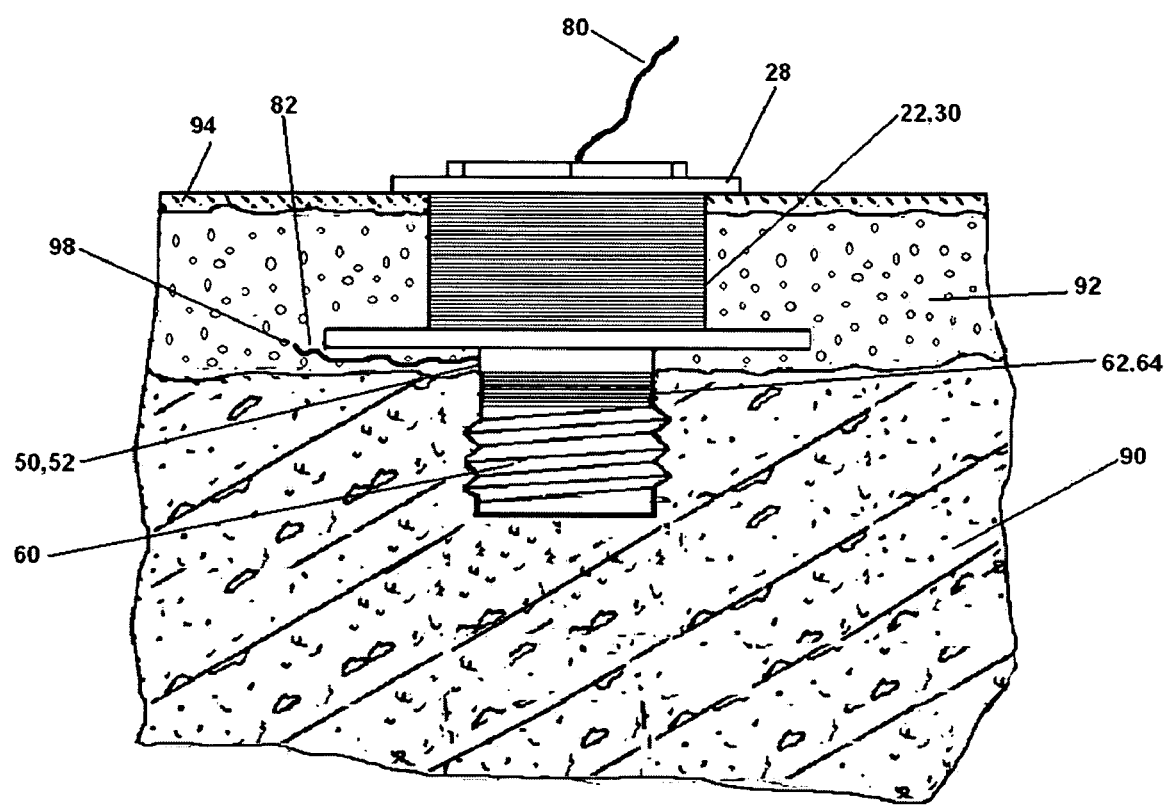
FIG. 5 is a schematic view showing the transcutaneous port of FIG. 3 anchored in a site in a patient's body.

In a further aspect, the present invention is directed to a method of providing a stable neural interface to a prosthesis using the transcutaneous port of the present invention. As shown in FIG. 5, transcutaneous port 10 is surgically implanted into a site of a patient's body by threading bone fixation section 60 into bone 90, positioning transosseous collar portion 62 within the bone and subcutaneous port section 20 within subcutaneous soft tissue 92, and positioning top flange 28 outside the skin 94. A receiving end 82 of an electrically conductive wire 80 into is placed from axial channel 40 though transverse channel 50 exiting from exit 52 into the subcutaneous tissue 92. The receiving end 82 of the conductive wire 80 is positioned in contact with a neural signal source 98 for receiving and transmitting neural signals originated in the tissue. Then, an electrode from a prosthetic motor device (not shown) is connected to the conductive wire 80 outside the body. The neural signals originated from the neural signal source 98 inside the tissue can be transmitted to the prosthetic motor device through conductive wire 80, can be used for activating or controlling a prosthetic motor device. FIG. 25 shows a photograph of transcutaneous port 10 in situ implanted in a rat.

The term "neural signal source" used herein includes, but is not limited to, muscles, nerves, and lesioned peripheral nerves due to amputation. It should be understood that various muscles in the soft tissues are rich in nerve density, and hence these muscles can be used as neural signal source.

It can be appreciated that the transcutaneous port of the present invention can also be used as a communication platform for transmitting electrical signals from outside into a location inside the body for stimulation.

Figure 6:
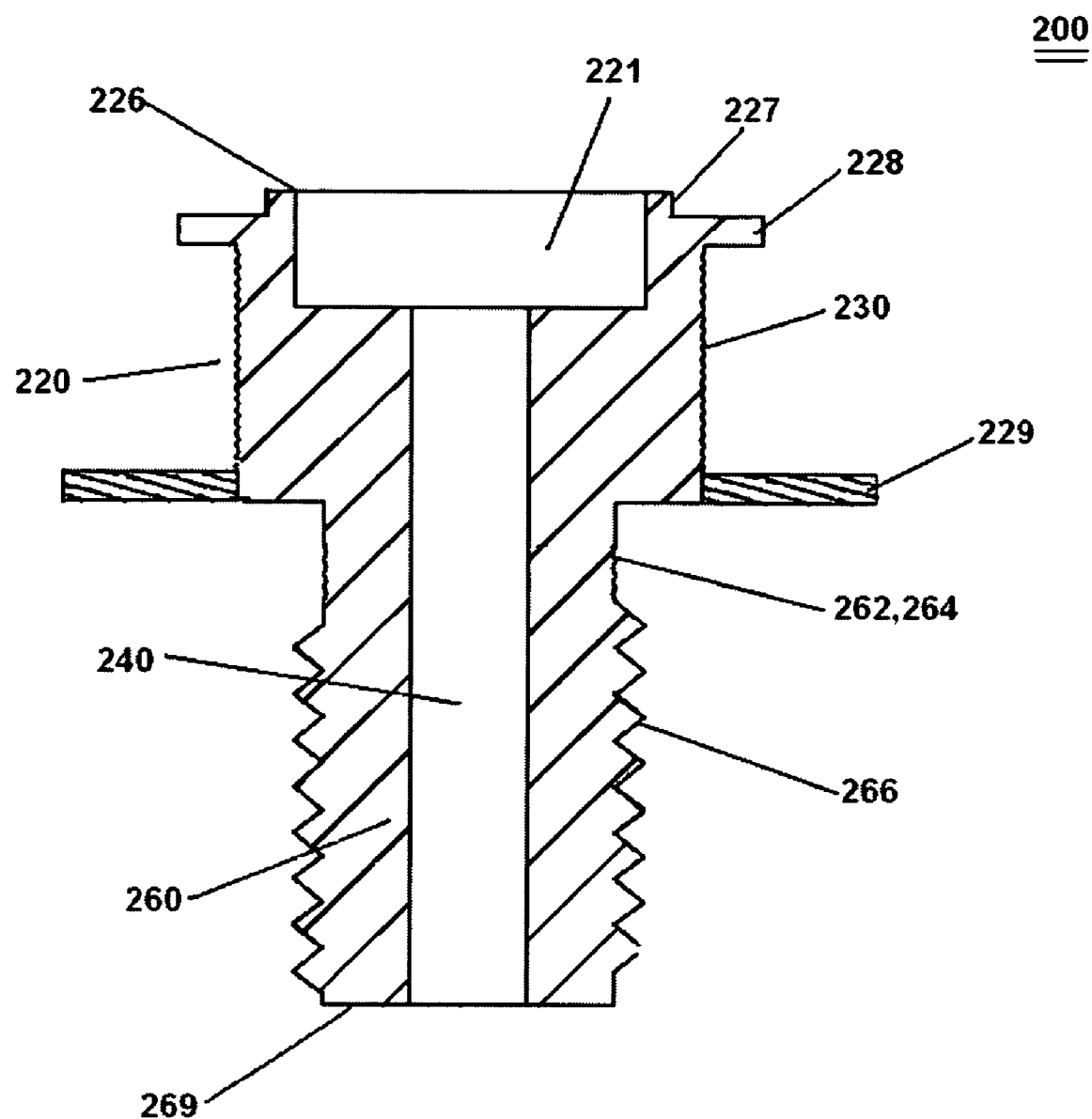
FIG. 6 is a cross sectional view of the transcutaneous port of another embodiment of the present invention.
Figure 7:
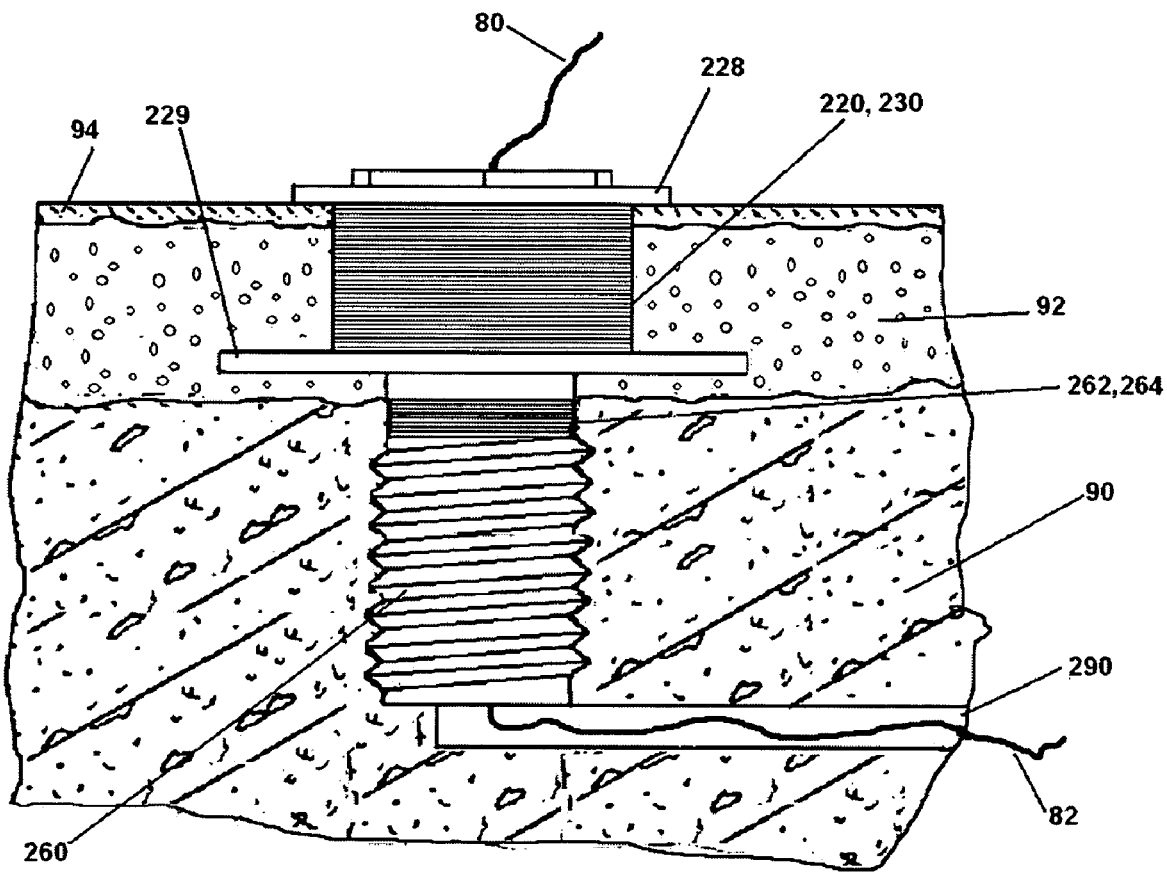
FIG. 7 is a schematic view showing the transcutaneous port of FIG. 6 anchored in a site in a patient's body.

In a further embodiment, the present invention provides a transcutaneous port 200 as shown in FIGS. 6 and 7. Transcutaneous port 200 comprises a subcutaneous section 220, bone fixation section 260 integrally extending from subcutaneous section 220, and an axial channel 240 extending from an upper end 226 of subcutaneous section 220 to a lower end 269 of bone fixation section 260. Subcutaneous section 220 has a top flange 228, a middle flange 229, and a top chamber 221 for receiving a cap to seal axial channel 240 from the exterior.

Subcutaneous section 220 has a first micro-textured external surface 230 which comprises a multiplicity of alternating microgrooves 4 and ridges 6. Bone fixation section 260 has a transosseous collar portion 262 and a threaded shaft portion 266. Transosseous collar portion 262 has a second micro-textured external surface 264, which comprises a multiplicity of alternating microgrooves 4 and ridges 6. The first and second micro-textured external surfaces 230 and 264 are the same as the first and second micro-textured external surfaces 30 and 64, respectively, which are described above in transcutaneous port 10.

As shown in FIG. 7, using transcutaneous port 200, the conductive wire 80 can be inserted through axial channel 240 all the way into bone. The receiving end 82 of conductive wire 80 can exit the bone from a bone channel 290 underneath the implant site of the transcutaneous port, and into a neural signal source.

The transcutaneous port of the present invention has substantial advantages over the existing transcutaneous port known in the art. Several structural features are implanted together on the transcutaneous port to provide stability for long term use of the transcutaneous port. More specifically, threaded shaft portion of bone fixation section anchors the transcutaneous port into bone. Middle flange substantially increases the contact areas between tissue and the transcutaneous port. More importantly, the first and second micro-textured external surfaces in subcutaneous port section and bone fixation section, respectively, enhance integrations of the soft tissue and bone tissue with the transcutaneous port, thereby providing two zones of strong integration. Such integration reduces microbial infiltration of the soft tissue site and establishes an interface between the transcutaneous port and the tissue, which can survive the amputation prosthetic environment.

While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents.

What is claimed is:

1. A transcutaneous port comprising:
   (a) a substantially cylindrical subcutaneous port section configured to be positioned within subcutaneous soft tissue, said subcutaneous port section comprising a lower portion and an upper portion larger in diameter than said lower portion, said upper portion of said subcutaneous port section having a first micro-textured external surface comprising a multiplicity of alternating microgrooves and ridges having a width in a range from about 4 to about 40 microns, and a depth in a range from about 4 to about 40 microns; said subcutaneous port section including an axial channel having an upper opening in said upper portion and extending into said lower portion; said lower portion having therein a transverse channel disposed transversely to, and connecting with, said axial channel; said transverse channel having an exit at one side of said lower portion of said subcutaneous port section, and said axial channel and transverse channel being adapted to house a conductive wire therethrough from said upper opening of said axial channel to said exit of said transverse channel; and
   (b) a substantially cylindrical bone fixation section configured to be positioned within bone tissue, said bone fixation section integrally extending from and underneath said lower portion of said subcutaneous port section; said bone fixation section comprising a transosseous collar portion having a second micro-textured external surface comprising a multiplicity of alternating microgrooves and ridges having a width in a range from about 4 to about 25 microns, and a depth in a range from about 4 to about 25 microns; and a threaded shaft portion underneath said transosseous collar portion, wherein said bone fixation section is devoid of transverse opening connecting with the axial channel of the subcutaneous port section.

2. The transcutaneous port of claim 1, wherein said subcutaneous port section further comprises a top flange disposed around an upper end of said upper portion.

3. The transcutaneous port of claim 1, wherein said subcutaneous port section further comprises a middle flange disposed around a low end of said upper portion.

4. The transcutaneous port of claim 1, wherein said upper portion of said subcutaneous port section further comprises a top chamber above said axial channel; and said top chamber has an internal thread for receiving a protective cap.

5. The transcutaneous port of claim 1, wherein said multiplicity of alternating microgrooves and ridges of said first and said second micro-textured external surfaces are in a direction perpendicular to a longitudinal axis of said transcutaneous port.

6. A method of providing a stable neural interface to a prosthesis comprising the steps of:
   (a) providing a transcutaneous port comprising:
      a substantially cylindrical subcutaneous port section configured to be positioned within subcutaneous soft tissue, said subcutaneous port section comprising a lower portion and an upper portion larger in diameter than said lower portion, said upper portion of said subcutaneous port section having a first micro-textured external surface comprising a multiplicity of alternating microgrooves and ridges having a width in a range from about 4 to about 40 microns, and a depth in a range from about 4 to about 40 microns; said subcutaneous port section including an axial channel having an upper opening in said upper portion and extending into said lower portion; said lower portion having therein a transverse channel disposed transversely to, and connecting with, said axial channel; said transverse channel having an exit at one side of said lower portion of said subcutaneous port section, and said axial channel and transverse channel being adapted to house a conductive wire therethrough from said upper opening of said axial channel to said exit of said transverse channel; and
      a substantially cylindrical bone fixation section configured to be positioned within bone tissue, said bone fixation section integrally extending from and underneath said lower portion of said subcutaneous port section; said bone fixation section comprising a transosseous collar portion having a second micro-textured external surface comprising a multiplicity of alternating microgrooves and ridges having a width in a range from about 4 to about 25 microns, and a depth in a range from about 4 to about 25 microns; and a threaded shaft portion underneath said transosseous collar portion, wherein said bone fixation section is devoid of transverse opening connecting with the axial channel of the subcutaneous port section;
   (b) surgically implanting said transcutaneous port into a site of a patient's body by anchoring said bone fixation section into a bone, positioning said transosseous collar portion within said bone, and said subcutaneous port section within subcutaneous soft tissue;
   (c) placing an electrically conductive wire into said axial channel and said transverse channel, and exiting a receiving end of said conductive wire from said exit of said transverse channel into said subcutaneous soft tissue and being contact with a neural signal source; and
   (d) connecting an electrode from said prosthesis to said conductive wire; thereby providing neural signals from said neural signal source through said conductive wire to said prosthesis.

* * * * *